(12) United States Patent
Rudie

(10) Patent No.: US 8,476,213 B1
(45) Date of Patent: Jul. 2, 2013

(54) SCRUB BARS AND METHODS FOR MAKING SAME

(76) Inventor: Monika S. Rudie, Dublin, OH (US)

( * ) Notice: Subject to any disclaimer, the term of this patent is extended or adjusted under 35 U.S.C. 154(b) by 0 days.

(21) Appl. No.: 13/488,260

(22) Filed: Jun. 4, 2012

Related U.S. Application Data

(60) Provisional application No. 61/493,125, filed on Jun. 3, 2011.

(51) Int. Cl.
*A61K 8/00* (2006.01)

(52) U.S. Cl.
USPC ............ 510/141; 510/152; 510/153; 510/463

(58) Field of Classification Search
USPC .......................................................... 510/141
See application file for complete search history.

(56) References Cited

U.S. PATENT DOCUMENTS

2006/0165622 A1* 7/2006 Hiramoto et al. ............... 424/65

* cited by examiner

*Primary Examiner* — Necholus Ogden, Jr.
(74) *Attorney, Agent, or Firm* — Lech Law, LLC; Robert R. Lech

(57) ABSTRACT

Scrub bars and methods for making scrub bars are disclosed. In some embodiments, the scrub bars comprise multiple layers.

3 Claims, 3 Drawing Sheets

SCRUB BARS AND METHODS FOR MAKING SAME

CROSS-REFERENCE TO RELATED APPLICATIONS

This application claims priority to U.S. Provisional Patent Application Ser. No. 61/493,125 entitled "Scrub Bars and Methods for Making Same" filed Jun. 3, 2011, which is incorporated by reference in its entirety as if fully set forth herein.

TECHNICAL FIELD

The present application generally relates to soap and scrub bars. More specifically, the present application relates to an odor reducing scrub bar.

BACKGROUND

Soap bars and scrub bars are well known. There is a need for a scrub bar that effectively reduces odor. There is a further need for a scrub bar that enables a user to control the intensity with which a target area may be scrubbed.

BRIEF DESCRIPTION OF THE DRAWINGS

The accompanying figures, which are incorporated in and constitute a part of the specification, illustrate various example articles, methods, and so on, and are used merely to illustrate various example embodiments. It should be noted that various components depicted in the figures may not be drawn to scale, and that the various elements, assemblies and designs depicted in the figures are presented for purposes of illustration only, and should not be considered in any way as limiting.

DETAILED DESCRIPTION

The present application describes various scrub bars and methods for making the various scrub bars. The scrub bars of the present application may comprise a single layer or a plurality of layers.

In a first example embodiment, an example single-layer scrub bar comprises a plurality of ingredients. The ingredients include a basic soap base. A variety of substances are acceptable for use as a soap base including, for example glycerin, goat milk, shea butter, cocoa butter, olive oil, mango butter, oatmeal, ultra white, marble base and honey. Additives may be added to the soap base. Suitable additives include, for example, essential oil, peppermint leaf, St. John's Wart, strawberry seed, blueberry seed, apricot seed, ground apricot kernel, poppy seed and coffee grounds.

The example single-layer scrub bar is designed to glide over a target area, such as the foot, while the internal ingredients provide an odor fighting scrub with varying degrees of intensity. The ingredients serve various specific purposes and enable varying degrees of scrub intensity to be applied to the target area. The varying degrees of scrub intensity enable a user to work on different levels of dry or chapped skin, such as the skin found on a human foot, for example.

Figure 1:
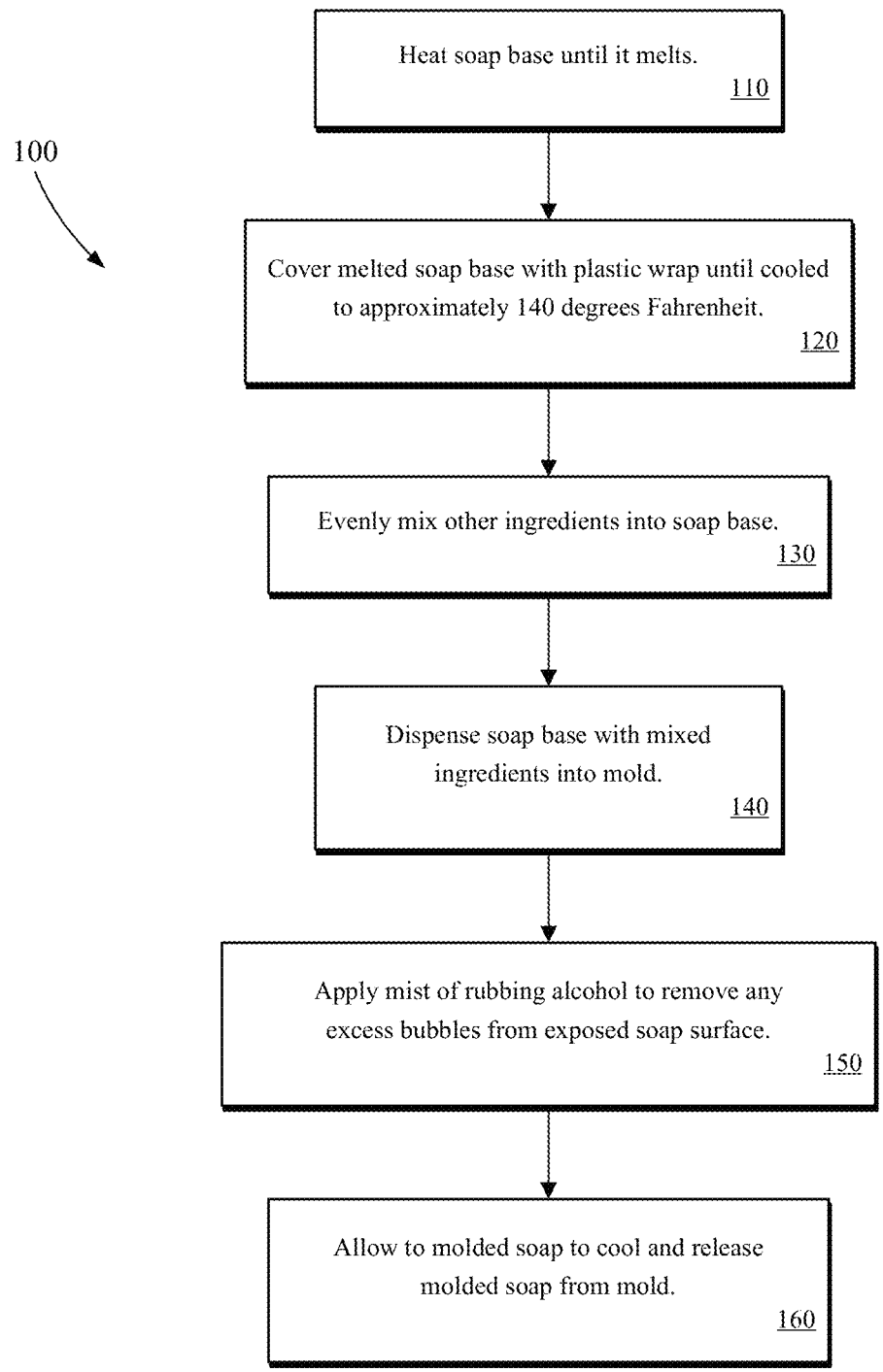
FIG. 1 is a flowchart illustrating an example method for making a single-layer scrub bar.

Referring now to FIG. 1, flowchart 100 illustrates an example methodology for making the example single-layer scrub bar. At block 110, a soap base is melted. The soap base may be any well known soap base, such as glycerin, for example. The soap base may be melted in any conventional way, such as using a microwave or double broiler.

As illustrated at block 120, once the soap base is melted, it is covered, such as with plastic wrap, until it is cooled to approximately 140 degrees Fahrenheit. Once the soap base has cooled to the desired temperature, other ingredients may be added. The other ingredients are evenly mixed into the soap base as shown at block 130 to create a scrub mixture. One example scrub mixture may be made using the ingredients set forth in Table I, below.

TABLE I

First Example Embodiment of Scrub Bar

| Ingredient | Amount |
| --- | --- |
| Soap base | 2 Pounds |
| Oil | 1-3 teaspoons |
| St. John's Wart | 1.5-2.0 Cups |
| Dried Peppermint Leaf | 1 cup |
| Strawberry seed | ⅓ cup |
| Poppy seed | ¼ cup |
| Blueberry seed | ¼ cup |
| Apricot seed | ¼ cup |
| Apricot kernel | ¼ cup |

At block 140, the soap base and evenly mixed ingredients comprising the scrub mixture are dispensed into one or more molds. Of course, the molds will retain the liquid scrub mixture to enable it to harden into in desired shapes and sizes. At block 150, a mist of rubbing alcohol is applied to the exposed surface of the liquid scrub mixture in each mold. The application of rubbing alcohol enables excess bubbles to be removed from the liquid scrub mixture.

The liquid scrub mixture is allowed to cool and solidify into a scrub bar, and the scrub bar may be released from the mold, as illustrated at block 160. Once removed, the scrub bar may be packaged accordingly.

Figure 2:
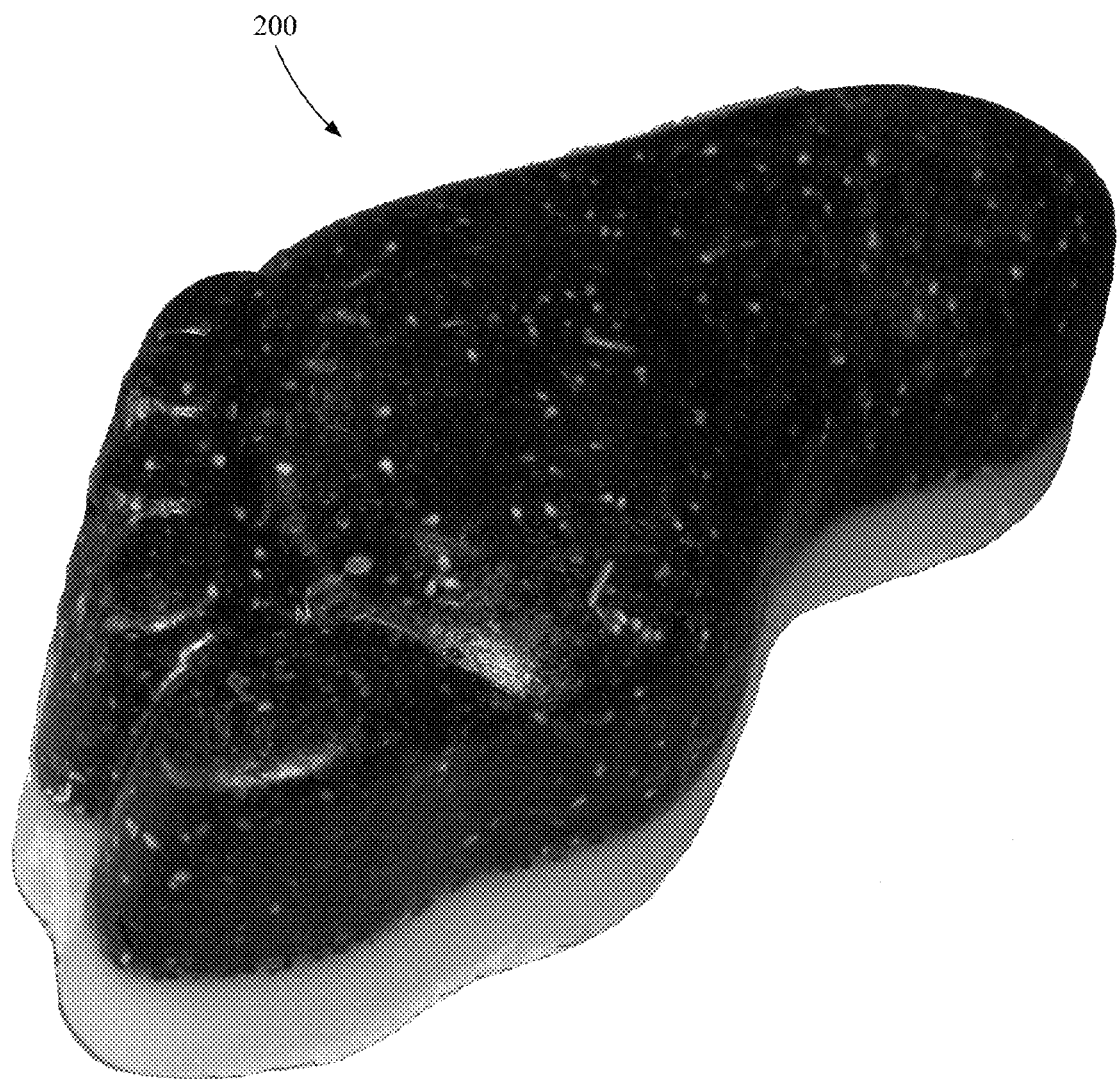
FIG. 2 is a perspective view of an example dual-layer scrub bar.
Figure 3:
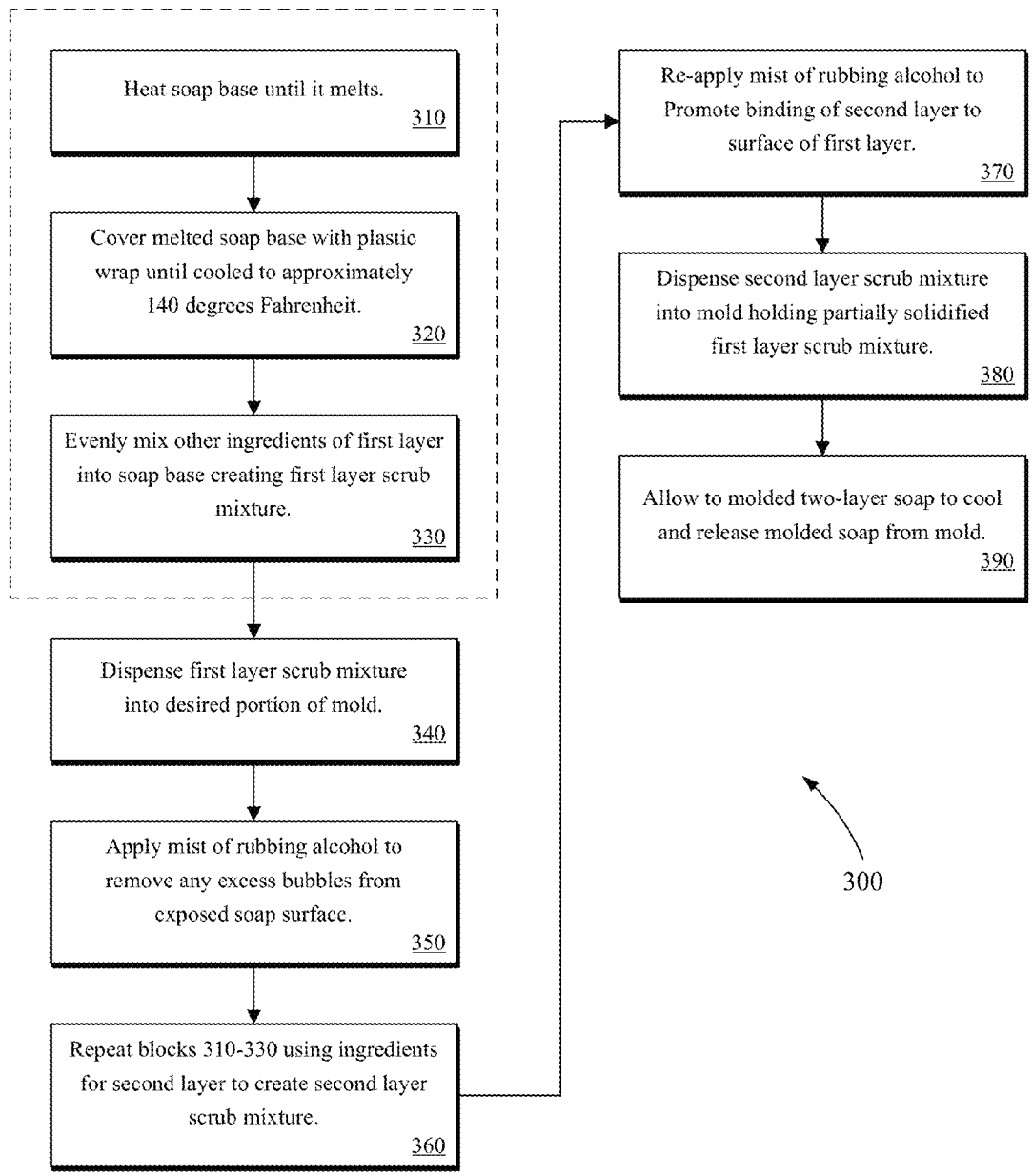
FIG. 3 is a flowchart illustrating an example method for making a dual-layer scrub bar.

An example dual-layer scrub bar 200 is illustrated in FIG. 2. Referring now to FIG. 3, flowchart 300 illustrates an example methodology for making the example dual-layer scrub bar 200. At block 310, a soap base is melted. As previously described with reference to FIG. 1, the soap base may be any well known soap base, such as glycerin, for example. The soap base may be melted in any conventional way, such as using a microwave or double broiler.

As illustrated at block 320, once the soap base is melted, it is covered, such as with plastic wrap, until it is cooled to approximately 140 degrees Fahrenheit. Once the soap base has cooled to the desired temperature, other ingredients may be added. The other ingredients are evenly mixed into the soap base as shown at block 330 to create a first layer scrub mixture.

At block 340, the first layer scrub mixture is dispensed into one or more molds. The first layer scrub mixture is only dispensed into a portion of each mold to enable each mold to also hold a second layer scrub mixture. At block 150, a mist of rubbing alcohol, or other suitable substance, is applied to the exposed surface of the liquid first layer scrub mixture in each mold. The application of rubbing alcohol enables excess bubbles to be removed from the liquid first layer scrub mixture.

Blocks 310-330 disclose the steps for making a first layer scrub mixture. Steps 310-330 are repeated at block 360 using ingredients for making a second layer scrub mixture. Example first layer and second layer scrub mixtures may be made using the ingredients set forth in Tables II and III, below.

TABLE II

Second Example Embodiment of Scrub Bar (Layer One)

| Ingredient | Amount |
|---|---|
| Soap base | 2 Pounds |
| Oil | 1-3 teaspoons |
| St. John's Wart | 1.5-2.0 Cups |
| Peppermint leaf | 1 cup |
| Strawberry seed | ⅓ cup |
| Poppy seed | ¼ cup |
| Blueberry seed | ¼ cup |
| Apricot seed | ¼ cup |
| Apricot kernels | ¼ cup |

TABLE III

Second Example Embodiment of Scrub Bar (Layer Two)

| Ingredient | Amount |
|---|---|
| Soap base | 2 Pounds |
| Apricot seed | ¼ cup |
| Apricot kernels | ⅝ cup |
| Blueberry seed | ½ cup |
| Colloidal oatmeal | ¼ cup |
| Stone ground oats | ⅙-¼ cup |

At block 370, a second mist of rubbing alcohol is applied to the exposed surface of the liquid first layer scrub mixture in each mold. The reapplication of rubbing alcohol promotes binding of the second layer to the first layer.

After the first layer scrub mixture has partially solidified, but while the first layer is still warm, the second layer scrub mixture is dispensed into each mold to complete each dual-layer scrub bar. Both layers of the scrub bar are to cool and solidify to form the dual-layer scrub bar, and the dual-layer scrub bar may be released from the mold, as illustrated at block 390. Once removed, the dual-layer scrub bar may be packaged accordingly.

Of course, one of ordinary skill in the art will recognize that the methodology for making the first and second example scrub bars includes measuring the various amounts of soap base, goat milk, shea butter, cocoa butter, olive oil and honey. The measurements disclosed herein are based on the using two pounds of soap base, but other quantities can be made using equivalent proportions of the ingredients.

Set forth below are various alternate embodiments for use in making the single layer and dual-layer scrub bars of the present application:

TABLE IV

Third Example Embodiment of Scrub Bar

| Ingredient | Amount |
|---|---|
| Soap base | 2 Pounds |
| Oil | 1-3 teaspoons |
| St. John's Wart | 1.5-2.0 Cups |
| Dried Peppermint Leaf | 1 cup |
| Strawberry seed | ⅓ cup |
| Poppy seed | ¼ cup |
| Blueberry seed | ¼ cup |
| Apricot seed | ¼ cup |
| Apricot kernels | ¼ cup |
| Coffee grounds | ¼-⅓ cup |

TABLE V

Fourth Example Embodiment of Scrub Bar (Layer One)

| Ingredient | Amount |
|---|---|
| Soap base | 2 Pounds |
| Oil | 1-3 teaspoons |
| St. John's Wart | 1.5-2.0 Cups |
| Dried Peppermint Leaf | 1 cup |
| Strawberry seed | ⅓ cup |
| Poppy seed | ¼ cup |
| Blueberry seed | ¼ cup |
| Apricot seed | ¼ cup |
| Apricot kernels | ¼ cup |
| Coffee grounds | ¼-⅓ cup |

TABLE VI

Fourth Example Embodiment of Scrub Bar (Layer Two)

| Ingredient | Amount |
|---|---|
| Soap base | 2 Pounds |
| Apricot seed | ¼ cup |
| Apricot kernels | ⅝ cup |
| Blueberry seed | ½ cup |
| Colloidal oatmeal | ⅙-¼ cup |
| Stone ground oats | ⅙-¼ cup |
| Coffee grounds | ¼-⅓ cup |

TABLE VII

Fifth Example Embodiment of Scrub Bar (Layer One)

| Ingredient | Amount |
|---|---|
| Soap base | 2 Pounds |
| Oil | 1-3 teaspoons |
| St. John's Wart | 1.5-2.0 Cups |
| Dried Peppermint Leaf | 1 cup |
| Strawberry seed | ⅓ cup |
| Poppy seed | ¼ cup |
| Blueberry seed | ¼ cup |
| Apricot seed | ¼ cup |
| Apricot kernels | ¼ cup |
| Coffee grounds | ¼-⅓ cup |

TABLE VIII

Fifth Example Embodiment of Scrub Bar (Layer Two)

| Ingredient | Amount |
|---|---|
| Soap base | 2 Pounds |
| Colloidal oatmeal | ⅛-¼ cup |
| Fruit extract (may include one or a combination of super fruits and/or may include banana leaf powder) | <5% |

TABLE VIII-continued

Fifth Example Embodiment
of Scrub Bar (Layer Two)

| Ingredient | Amount |
| --- | --- |
| Ground oats | ⅛ cup |
| Goat milk powder | ⅛ cup |
| Primrose oil | 30 ml |
| Hemp oil | 30 ml |

TABLE IX

Sixth Example Embodiment
of Scrub Bar (Layer One)

| Ingredient | Amount |
| --- | --- |
| Soap base | 2 Pounds |
| Oil | 1-3 teaspoons |
| St. John's Wart | 1.5-2.0 Cups |
| Dried Peppermint Leaf | 1 cup |
| Strawberry seed | ⅓ cup |
| Poppy seed | ¼ cup |
| Blueberry seed | ¼ cup |
| Apricot seed | ¼ cup |
| Apricot kernels | ¼ cup |

TABLE X

Sixth Example Embodiment
of Scrub Bar (Layer Two)

| Ingredient | Amount |
| --- | --- |
| Soap base | 2 Pounds |
| Colloidal oatmeal | ½ cup |
| Ground adzuki beans | 1 cup |
| Fruit extract | teaspoon |

Unless specifically stated to the contrary, the numerical parameters set forth in the specification are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the articles of manufacture, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A scrub bar comprising:
   soap base;
   oil;
   St. John's wart;
   dried peppermint leaf;
   strawberry seed
   poppy seed;
   blueberry seed;
   apricot seed; and
   coffee grounds.
2. A scrub bar comprising:
   a first layer, the first layer comprising:
      soap base,
      oil,
      St. John's wart,
      dried peppermint leaf,
      strawberry seed,
      poppy seed,
      blueberry seed,
      apricot seed, and
      coffee grounds; and
   a second layer, the second layer comprising:
      soap base,
      apricot seed,
      apricot kernels,
      blueberry seed,
      colloidal oatmeal,
      stone ground oats, and
      coffee grounds.
3. A scrub bar comprising:
   a first layer, the first layer comprising:
      soap base,
      oil,
      St. John's wart,
      dried peppermint leaf,
      strawberry seed,
      poppy seed,
      blueberry seed,
      apricot seed, and
      apricot kernels,
   a second layer, the second layer comprising:
      soap base,
      colloidal oatmeal,
      goat milk powder,
      ground oats, fruit extract (combination of super fruits and banana leaf powder),
primrose oil, and
hemp oil.

* * * * *